United States Patent [19]

Dagani

[11] 4,333,878

[45] Jun. 8, 1982

[54] PROCESS FOR PRODUCING SUBSTITUTED PYRROLES

[75] Inventor: Michael J. Dagani, Baton Rouge, La.

[73] Assignee: Ethyl Corporation, Richmond, Va.

[21] Appl. No.: 236,039

[22] Filed: Feb. 19, 1981

Related U.S. Application Data

[63] Continuation-in-part of Ser. No. 137,510, Apr. 4, 1980, abandoned.

[51] Int. Cl.³ .......................................... C07D 207/34
[52] U.S. Cl. ..................................................... 548/531
[58] Field of Search ................................... 260/326.46

[56] References Cited

U.S. PATENT DOCUMENTS

| 3,752,826 | 8/1973 | Carson | 260/326.46 |
| 3,865,840 | 2/1975 | Carson | 260/326.46 |
| 3,952,012 | 4/1976 | Carson | 260/326.46 |
| 4,048,191 | 9/1977 | Carson | 260/326.46 |

OTHER PUBLICATIONS

Hantzch; *Berichte der Deutschen Chemischen Gesellschaft;* pp. 1474–1479 (1890).
Foerst; *Ullmanns Encycl. der Technischen Chemie;* Band 3, pp. 42–43 (1953); *Beilstein Handbuch der Organischen Chemie;* Third Vol.; p. 791 (1921).
Grob et al.; Fasciculusi; vol. XXXVI, pp. 49–58 (1953).
Jones et al.; The Chemistry of Pyrroles, p. 65 (1977).

*Primary Examiner*—Mary C. Lee
*Attorney, Agent, or Firm*—Donald L. Johnson; John F. Sieberth; Willard G. Montgomery

[57] ABSTRACT

A process for the preparation of 1,4-dialkyl-pyrrole diesters by reacting the enamine of a dialkyl acetone dicarboxylate with a 2-hydrocarboxy-1-nitroalkane.

8 Claims, No Drawings

PROCESS FOR PRODUCING SUBSTITUTED PYRROLES

CROSS REFERENCE TO RELATED APPLICATION

This application is a continuation-in-part of application Ser. No. 137,510, filed Apr. 4, 1980 now abandoned.

BACKGROUND OF THE INVENTION

This invention relates to a process for producing substituted pyrroles, especially pyrrole-2-acetic acids and derivative compounds thereof. More particularly, the process of this invention is concerned with processes which produce 1,4-diloweralkyl-3-loweralkoxycarbonyl-pyrrole-2-acetate which is a useful intermediate for analgesic and anti-inflammatory pharmaceutical compounds.

It has been found difficult in the past to substitute pyrrole rings, which already contain substituents at other positions in the ring, at the 4-position because of steric hindrance and ring deactivation. Thus, Carson, U.S. Pat. No. 3,752,826 and U.S. Pat. No. 3,865,840, teach the preparation of certain 4-substituted 5-aroylpyrrole alkanoic acids and the corresponding salts, esters, nitriles, amides and substituted amides thereof represented by the formulas:

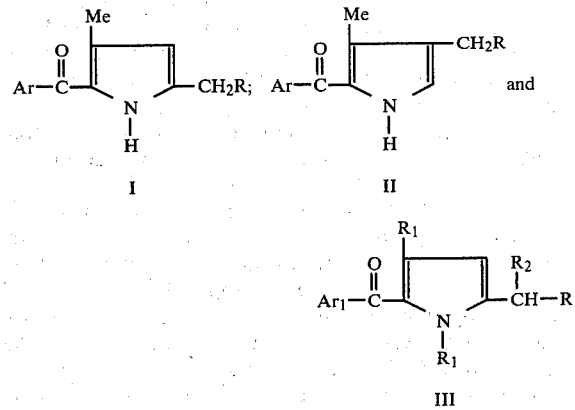

wherein:
Ar represents a member selected from the group consisting of phenyl, monosubstituted phenyl and polysubstituted phenyl, each substituent of said substituted phenyls being a member selected from the group consisting of halo, lower alkyl and lower alkoxy;

$Ar_1$ represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano, and methylthio;

R represents a member selected from the group consisting of COOH, COO-(lower alkyl), $CONH_2$, CONH-(lower alkyl) and CON-(lower alkyl)$_2$;

$R_1$ represents lower alkyl;

$R_2$ represents a member selected from the group consisting of hydrogen and lower alkyl, provided that when said Ar, is a member of the group consisting of nitrosubstituted phenyl, then, with regard to Formula III, $R_2$ is hydrogen;

Me is methyl;

and the non-toxic, therapeutically acceptable salts of such acids, such as are obtained from the appropriate organic and inorganic bases. According to Carson, supra, the 4-substituted 5-aroylpyrrole alkanoic acids must be obtained by condensation of the appropriate 1-aryl-1,2,3-butanetrione-2-oxime and an appropriate dialkyl acetonedicarboxylate as starting materials to provide the corresponding ring closed pyrrole, alkyl 5-aroyl-3-alkoxycarbonyl-4-methylpyrrole-2-acetate; or by condensation of an appropriate chloromethyl loweralkyl ketone added to a mixture of an appropriate di-loweralkyl acetonedicarboxylate, preferably the diethyl ester and a loweralkyl amine to provide the ring-closed pyrrole, alkyl 1-loweralkyl-4-loweralkyl-3-alkoxycarbonyl-pyrrole-2-acetate. These pyrrole intermediates are then treated as disclosed in U.S. Pat. Nos. 3,752,826 and 3,865,840 to obtain the desired 5-aroyl-4-lower alkyl-pyrrole-2-alkanoic acids and acid derivatives thereof useful as anti-inflammatory agents.

The condensation of chloromethylketone, ammonia and hydroxy crotonic acid alkylester through an anti-crotonic acid ester is taught by Fischer and Orth, *Die Chemie Des Pyrroles*, pp. 5–6 and 233–234, Edward Brothers, Inc., Ann Arbor, Mich., 1943. However, neither the 4-alkyl-substituent nor the diester functionality are disclosed in this reference.

Another pyrrole ring-closure synthesis, known as the Hantzsch pyrrole synthesis, teaches the interaction of alphachloro-aldehydes or ketones with beta-ketoesters and ammonia or amines to give pyrroles, Gowan and Wheeler, *Name Index of Organic Reactions*, p. 116, Longmans, Green and Co., Ltd., New York, N.Y., 1960.

In a similar manner, there is taught the reaction of chloroacetone with a salt produced from reaction of methyl amine and diethyl acetone dicarboxylate to give a 4-methylpyrrole, Jones and Bean, *The Chemistry of Pyrroles*, p. 59, 104, Academic Press, Inc., New York, 1977. Also, the pyrrole synthesis from chloromethyl ketones and beta-ketocarboxylic esters with ammonia or amines is known, Krauch and Kunz, Organic Name Reactions, p. 211, John Wiley and Sons, Inc., New York, 1964. However, such teachings either fail to suggest the possibility of the pyrrole diester compounds or teach no more than Carson, supra, and are based thereon.

In Grob, C. A. and Camenisch, K., *Helv. Chimica Acta* 36, No. 8, pp. 49–58 (1953), there is disclosed a method for preparing a pyrrole ring by condensing a nitropropene and a reaction product of an amine with acetoacetate. The reaction product must be dehydrogenated to close the ring and form the pyrrole.

Thus, from the teachings of the prior art, processes for preparation of pyrroles having 4-alkyl substituents and diester functionality can be vastly improved to provide processes with higher yields and increased purity. Particularly, it would be desirable to have a selective process for producing 4-alkyl substituted pyrrole diesters in which there are no 5-alkyl substituents. Further, it would be advantageous to employ a process using more nearly stoichiometric amounts of reactants. Finally, it would be still further advantageous to carry out the exothermic reaction in such a manner as to mitigate the effects of exothermic reaction. These objectives and advantages, as well as others, can be achieved by the process of the invention described hereinbelow.

THE INVENTION

The process of the invention is based on the discoveries that the reaction of certain carboxy nitroalkanes with the enamine of acetone dicarboxylate causes cyclization or condensation to occur, forming a 4-alkyl-substituted pyrrole diester, whereas reaction of the enamine with chloroacetone has no appreciable effect. Accordingly, it was entirely unexpected that the present invention provides a process for the preparation of a loweralkyl 1,4-diloweralkyl-3-loweralkoxy carbonyl-pyrrole-2-acetate of the formula:

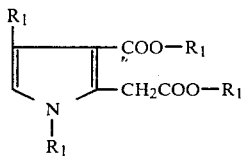

wherein each $R_1$ is independently selected from a lower alkyl group which comprises reacting a mixture of a loweralkyl enamine of a diloweralkyl acetone dicarboxylate of the formula:

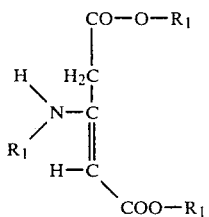

with a compound of formula:

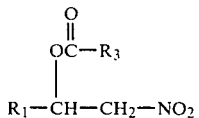

wherein $R_1$ is independently selected and has the same meaning as hereinabove and $R_3$ is a lower alkyl, tolyl or benzyl group.

As used herein, "lower alkyl" and "lower alkoxy" may be straight or branch chained saturated hydrocarbons having from 1 to 6 carbon atoms, such as, for example, methyl, ethyl, propyl, isopropyl, butyl, pentyl, hexyl, and the like alkyls, and, respectively, the corresponding alkoxys such as methoxy, ethoxy, propoxy, isopropoxy, etc.

Preferably, the process includes the reaction of the methyl enamine of diethyl acetone dicarboxylate with acetoxy nitroalkane, optionally in the presence of a solvent, to form a 4-alkyl or 1,4-dialkyl pyrrole 3-ethoxycarbonyl-pyrrole-2-acetate acid ethyl ester, depending upon the reactants employed.

The compounds of Formula IV in which $R_1$ is a lower alkyl group are prepared from an appropriate lower alkyl enamine of a dilower alkyl acetone dicarboxylate of Formula V and a compound of Formula VI. Accordingly, in an illustrative procedure the enamine is prepared by reaction of methyl amine with acetone dicarboxylic acid in a suitable solvent, such as ethanol or methanol, forming a carbinol amine followed by evaporation of the solvent and heating to dehydrate the carbinol amine to the corresponding enamine. The procedure was accomplished easily using 5 to 10 percent excess gaseous methyl amine.

The compounds of Formula VI are easily prepared by condensation of an appropriate aldehyde and a primary nitroalkane, catalyzed in the presence of aqueous base to produce a 1-nitroalkan-2-ol; followed by acylation of the 1nitroalkan-2-ol with an acyl chloride to afford the 2-hydrocarboxy-1-nitroalkane in good yield of isolated material. For example, the condensation of acetaldehyde and nitromethane catalyzed by sodium bicarbonate in water produced about 70 percent yield of 1-nitro-2-propanol which on acetylation of the neat 1-nitro-2-propanol with acetyl chloride produced 2-acetoxy-1-nitropropane in 90 percent yield of distilled material.

Exemplary of the 2-hydrocarboxy-1-nitroalkanes useful in this invention are 2-acetoxy-1-nitropropane, 2-acetoxy-1-nitrobutane, 2-acetoxy nitropentane, 2-acetoxy-1-nitrohexane, 2-acetoxy-1-nitroheptane and 2-acetoxy-1-nitrooctane. Thus, when $R_3$ is methyl an acetoxy group is formed. However, $R_3$ can be ethyl, propyl, butyl, pentyl, hexyl, tolyl or benzyl. Since the hydrocarboxy group is a leaving group, it does not enter the final product and can, therefore, be any suitable hydrocarboxy group.

The cyclization reaction is accomplished by admixture of the appropriate enamine, prepared as indicated above, and the hydrocarboxy nitroalkane, optionally in the presence of a solvent, heating to elevated temperature and isolating the cyclized loweralkyl 1,4-diloweralkyl-3-loweralkoxy carbonyl-pyrrole-2-acetate produced. The progress of the reaction can be monitored easily by gas chromatographic analysis to determine the rate of reaction and yield.

The reaction can be conducted in a solvent, if desired, such as a polar non-acidic solvent. Excellent results are obtained using alcohols as solvents. Lower alcohols such as methanol, ethanol, isopropanol and the like can be employed. In addition, heterocyclic polar solvents, such as, tetrahydrofuran can also be employed. Amides such as dimethyl formamide and highly polar materials such as dimethyl sulfoxide can be employed. In addition, other non-reactive materials such as acetonitrile can also be used. Although solvents such as tetrahydrofuran and dimethyl sulfoxide can be employed, they may not be practical or as desirable because of lower polarity or tendency to react with the enamine or 2-hydrocarboxy-1-nitroalkane forming undesirable reaction products or polymer, lowering yields and increasing impurities or clean-up requirements. However, it has been found that solvent is not required and good yields of desired 4-substituted pyrrole diesters produced by the process of this invention without the use of a solvent.

The reaction can be carried out at temperature ranging from ambient up tp about 100° C. However, the reaction takes an inordinate amount of time at ambient temperatures whereas product and starting material degradation begins to occur at the higher temperatures. In general, it has been found that temperatures from about 50° to about 90° C. provide sufficient reaction rates. More specifically, from about 60° to about 90° C. is a more preferable temperature range for the process of the present invention. To a certain extent, the materials being reacted and the presence or absence of a solvent will have some relationship to the temperature. However, temperatures from about 75° to about 90° C. have been employed to produce best results. The reaction occurs over a period of from about ½ to greater than 200 hours. However, time is not a truly independent variable, depending to a certain extent on the reaction temperature and the amount of starting materials. Further, it is not critical to add the reactants in any particular mode or fashion. However, it would not be desirable to heat the 2-hydrocarboxy-1-nitropropane to reaction temperature for long periods of time. It is believed that the best results would be obtained, however, if the 2-hydrocarboxy-1-nitropropane were added to the enamine which is maintained at reaction temperature. According to the process of the present invention, in general, the best procedure is to mix the methyl enamine of acetone dicarboxylate and 2-acetoxy-1-nitropropane and heat the mixture to 90° with continued mixing under a nitrogen atmosphere. The presence of an internal standard such as dibutyl phthalate is useful to follow the progress of the reaction for analytical purposes. After reaction for 2 hours, analysis shows 66 percent yield of the corresponding diethyl 1,4-dimethyl-3-ethoxy carbonyl pyrrole-2-acetate.

It has been found that the proportions of the reactants can be varied with some degree of latitude without greatly affecting the practicality of the process. For instance, an excess of 5 to 200 percent in the enamine can be employed with from about 10 to about 60 percent excess enamine being preferred for the diethyl ester and from about 10 to about 200 percent excess of the enamine being preferred for the dimethyl ester. Also, the reaction can be carried out in the presence of excess 2-hydrocarboxy-1-nitroalkane, for instance from about 30 to about 50 percent excess of the 2-hydrocarboxy-1-nitroalkane. The excesses referred to are molar equivalent excess and are expressed as a percentage of the stoichiometric amount. In view of the ability to obtain the desired reaction with an excess of either reactant, there is no requirement for an excess of either. However, it is preferred to use an excess of the enamine reactant because liberated acetic acid would tend to react with the enamine and thus decrease its availability for reaction with the 2-hydrocarboxy-1-nitroalkane.

The above 4-substituted pyrrole diester compounds can then be converted into the desired 4-substituted 5-aroyl-pyrrole alkanoic acids and derivatives thereof according to the teachings of U.S. Pat. Nos. 3,752,826 and 3,865,840, which are incorporated herein by reference as if fully set forth.

The following examples are intended to illustrate, not to limit, the scope of the present invention.

EXAMPLE 1

A. Preparation of N-methyl enamine of diethyl acetone dicarboxylate

To 88.9 grams (0.44 mol) of diethyl acetone dicarboxylate in 300 milliliters of diethyl ether was added 14.1 grams (0.454 mol) of methyl amine in 65 grams of methanol. Solids formed during the addition, preventing stirring during the last one-half of the methyl amine addition. The solids were filtered, washed with methanol and vacuum oven dried at 45° C. overnight. A yellow liquid formed the next morning, was separated and analyzed as a mixture of the ketamine and the enamine.

Analysis of the dried solids by vapor phase chromatography using 10% SE-52 column A programmed at 8°/minute from 100° C. showed a small amount of starting diester and a major peak at 16.43 minutes (98 area percent).

B. Preparation of 1,4-dimethyl-3-carbethoxy-pyrrole-2-acetic acid ethyl ester

A mixture of N-methyl enamine of diethyl acetone dicarboxylate (1.052 grams, 4.72 millimols) and 2-acetoxy-1-nitropropane (0.4303 grams, 2.93 millimols) was heated at 90° C. in a nitrogen atmosphere in the presence of 0.1246 grams of dibutyl phthalate as an internal standard. Analysis by vapor phase chromatography after 2 hours showed 1.94 millimols of 1,4-dimethyl-3-carbethoxy-pyrrole-2-acetic acid ethyl ester of 66 percent yield.

In a manner similar to Example 1 above, a number of experiments were carried out varying the temperatures, reaction time, solvent, ratio of reactants and alkyl group on the dialkyl acetone diacetate. The results were analyzed by vapor phase chromatography with internal standard and are shown in Table I.

TABLE I

Preparation of 1,4-Dimethyl-3-Carbethoxy-Pyrrole-2-Acetic Acid Esters

| Example No. | % Excess | (ADC-EA or ANP)* | Solvent** | Temp. (°C.) | Time (hr) | % Yield |
|---|---|---|---|---|---|---|
| Diethyl Ester | | | | | | |
| 2 | 20 | ADC-EA | EtOH | 78 | 5 | 66 |
| 3 | 5 | ADC-EA | MeOH | 65 | 5 | 58 |
| 4 | 2.5 | ADC-EA | EtOH(NaHCO$_3$) | 78 | 5 | 17 |
| 5 | 14 | ADC-EA | IPA | 82 | 5 | 58 |
| 6 | 14 | ADC-EA | EtOH | 78 | 2.5 | 60 |
| 7 | 14 | ADC-EA | THF | 66 | 3.5 | —(5% Conv.) |
| 8 | 14 | ADC-EA | THF/H$_2$O(NaHCO$_3$) | 70 | 1 | <5 (95% Conv.) |
| 9 | 36 | ADC-EA | EtOH | 78 | 1.3 | 57 |
| 10 | 13 | ADC-EA | EtOH | 25 | 2.5 | 53 |
| 11 | 13 | ADC-EA | EtOH(NaHCO$_3$) | 25 | 18 | 18 |
| 12 | 10 | ADC-EA | CH$_3$CN | 82 | 1.8 | 57 |
| 13 | 50 | ANP | EtOH | 78 | 2 | 37 |
| 14 | 20 | ADC-EA | DMF | 25 | 72 | 26 |
| 15 | 20 | ADC-EA | DMF | 110 | 0.8 | 32 |
| 16 | 20 | ADC-EA | DMSO | 25 | 24 | 8 |
| 17 | 20 | ADC-EA | MeOH | 65 | 5 | 25 |
| 18 | 37 | ANP | None | 75 | 0.5 | 53 |
| 19 | 42 | ANP | " | 60 | 1.5 | 54 |
| 20 | 20 | ADC-EA | " | 60 | 2 | 62 |
| 21 | 20 | ADC-EA | " | 60 | 2 | 60 |
| 22 | 42 | ADC-EA | " | 60 | 2 | 62 |

TABLE I-continued

Preparation of 1,4-Dimethyl-3-Carbethoxy-Pyrrole-2-Acetic Acid Esters

| Example No. | % Excess (ADC-EA or ANP)* | Solvent** | Temp. (°C.) | Time (hr) | % Yield |
|---|---|---|---|---|---|
| 23 | 42 | ANP | " | 60 | 2 | 47 |
| 24 | 10 | ADC-EA | " | 90 | 1 | 50 |
| 25 | 20 | ADC-EA | " | 90 | 1 | 57 |
| Dimethyl Ester | | | | | |
| 26 | 12 | ADC-EA | None | 53 | 1 | 54 |
| 27 | 11 | " | " | 53 | 3 | 59 |
| 28 | 11 | " | " | 53 | 2.8 | 61 |
| 29 | 20 | " | " | 70 | 1 | 65 |
| 30 | 25 | " | " | 25 | 24 | 63 |
| 31 | 25 | " | " | 25 | 42 | 65 |
| 32 | 100 | " | " | 75 | 0.7 | 73 |
| 33 | 100 | " | " | 75 | 1.3 | 74 |
| 34 | 200 | " | " | 75 | 1.5 | 73 |

*ADC-EA is abbreviation for dialkyl acetone dicarboxylate enamine; ANP is an abbreviation for 2-acetoxy-1-nitropropane.
**DMF is dimethyl formamide; DMSO is dimethyl sulfoxide.
**EtOH is ethanol; MeOH is methanol; IPA is isopropanol; THF is tetrahydrofuran.

It can be seen that wide variation in ratio of reactants, time, temperature, solvent and the like will cause varying results, but in all instances, product was detected.

From the above description of the process of this invention, one skilled in the art will be able to make variations and changes which are nevertheless within the scope of the invention. Therefore, it is desired that the process of this invention be limited only by the lawful scope of the appended claims.

What is claimed is:

1. A process for the preparation of a loweralkyl 1,4-diloweralkyl-3-loweralkoxycarbonyl-pyrrole-2-acetate of the formula:

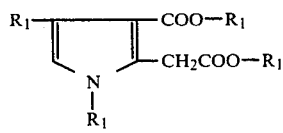

wherein each $R_1$ is independently a loweralkyl group which comprises reacting a mixture of a loweralkyl enamine of a diloweralkyl acetone dicarboxylate of the formula:

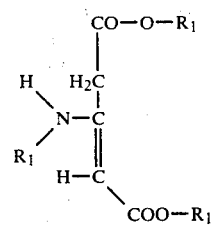

with a compound of the formula:

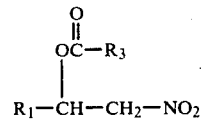

wherein $R_1$ is independently selected and has the same meaning as hereinabove and $R_3$ is a lower alkyl, tolyl or benzyl group.

2. The process of claim 1 wherein said dicarboxylate is the methyl enamine of diethyl acetone dicarboxylate.

3. The process of claim 1 wherein said dicarboxylate is the methyl enamine of dimethyl acetone dicarboxylate.

4. The process of claim 1 wherein said compound of Formula VI is 2-acetoxy-1-nitropropane.

5. The process of claim 1 wherein said dicarboxylate is the methyl enamine of diethyl acetone carboxylate and said compound of Formula VI is 2-acetoxy-1-nitropropane.

6. The process of claim 1 wherein said dicarboxylate is the methyl enamine of dimethyl acetone dicarboxylate and said compound of Formula VI is 2-acetoxy-1-nitropropane.

7. The process of claim 1 wherein said reacting is carried out over a period ranging from about 0.5 to about 42 hours at temperatures ranging from about 25° to about 110° C.

8. The process of claim 1 wherein said reacting is optionally carried out in the presence of a solvent.

* * * * *

UNITED STATES PATENT AND TRADEMARK OFFICE
CERTIFICATE OF CORRECTION

PATENT NO. : 4,333,878
DATED : June 8, 1982
INVENTOR(S) : Michael J. Dagani

It is certified that error appears in the above-identified patent and that said Letters Patent is hereby corrected as shown below:

Column 4, line 10, reads "1nitroalkan-2-ol", should read --1-nitroalkan-2-ol--.

Column 6, line 54, reads "EtOH(NaHCO)$_3$", should read --EtOH(NaHCO$_3$)--.

Signed and Sealed this

Twelfth Day of April 1983

[SEAL]

*Attest:*

*Attesting Officer*

GERALD J. MOSSINGHOFF

*Commissioner of Patents and Trademarks*